US011875888B2

(12) United States Patent
Inoue et al.

(10) Patent No.: US 11,875,888 B2
(45) Date of Patent: Jan. 16, 2024

(54) REHABILITATION ASSISTANCE DEVICE, REHABILITATION ASSISTANCE METHOD, AND NON-TRANSIENT STORAGE MEDIUM STORING REHABILITATION ASSISTANCE PROGRAM

(71) Applicant: OMRON HEALTHCARE Co., Ltd., Kyoto (JP)

(72) Inventors: Kosuke Inoue, Kyoto (JP); Tetsuya Sato, Kyoto (JP); Mika Kijimuta, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 212 days.

(21) Appl. No.: 17/447,128

(22) Filed: Sep. 8, 2021

(65) Prior Publication Data

US 2021/0398642 A1     Dec. 23, 2021

Related U.S. Application Data

(63) Continuation of application No. PCT/JP2020/006647, filed on Feb. 19, 2020.

(30) Foreign Application Priority Data

Mar. 13, 2019  (JP) ................. 2019-045931

(51) Int. Cl.
*G16H 20/30* (2018.01)
*G16H 40/67* (2018.01)
(Continued)

(52) U.S. Cl.
CPC ......... *G16H 20/30* (2018.01); *A63B 24/0075* (2013.01); *A63B 71/0622* (2013.01); *G16H 40/20* (2018.01); *G16H 40/67* (2018.01)

(58) Field of Classification Search
CPC ........ G16H 20/30; G16H 40/20; G16H 40/67; G16H 40/63; A63B 24/0075; A63B 71/0622
(Continued)

(56) References Cited

U.S. PATENT DOCUMENTS

2004/0038190 A1* 2/2004 Abraham-Fuchs .... G16H 70/20
434/262
2011/0098928 A1  4/2011 Hoffman et al.
(Continued)

FOREIGN PATENT DOCUMENTS

AU  2014280966 A1  5/2016
CN     1415271 A    5/2003
(Continued)

OTHER PUBLICATIONS

English translation of the Written Opinion of the International Searching Authority for International Application No. PCT/JP2020/006647, dated May 26, 2020.
(Continued)

*Primary Examiner* — Joy Chng
(74) *Attorney, Agent, or Firm* — Birch, Stewart, Kolasch & Birch, LLP

(57) ABSTRACT

To provide a rehabilitation assistance device, a rehabilitation assistance method, and a non-transient storage medium storing a rehabilitation assistance program that support continuous rehabilitation by enabling the generation of a rehabilitation plan that can increase the motivation to continue rehabilitation. When a patient selects one set from an activity event information DB that stores a plurality of sets that associate information of a predetermined activity event with information of an exercise amount for each of a plurality of body parts when the activity event is performed, the patient can check on the screen displayed on the display
(Continued)

unit to what extent the exercise amount contained in one's rehabilitation plan information is achieved by the activity event of the selected set.

5 Claims, 10 Drawing Sheets

(51) Int. Cl.
  *G16H 40/20* (2018.01)
  *A63B 24/00* (2006.01)
  *A63B 71/06* (2006.01)

(58) Field of Classification Search
  USPC .......................................................... 705/2–3
  See application file for complete search history.

(56) References Cited

U.S. PATENT DOCUMENTS

| | | | |
|---|---|---|---|
| 2011/0197157 A1 | 8/2011 | Hoffman et al. | |
| 2013/0211562 A1* | 8/2013 | Winter | A63B 24/0062 700/91 |
| 2013/0238287 A1 | 9/2013 | Hoffman et al. | |
| 2015/0325130 A1 | 11/2015 | Baek et al. | |
| 2015/0325139 A1* | 11/2015 | Kang | A61B 5/7271 434/236 |
| 2016/0220865 A1 | 8/2016 | Seo | |
| 2016/0317867 A1 | 11/2016 | Hoffman et al. | |
| 2017/0259119 A1 | 9/2017 | Hoffman et al. | |
| 2020/0215392 A1 | 7/2020 | Hoffman et al. | |
| 2021/0205665 A1 | 7/2021 | Hoffman et al. | |

FOREIGN PATENT DOCUMENTS

| | | | |
|---|---|---|---|
| CN | 102314557 A | 1/2012 | |
| CN | 105683871 A | 6/2016 | |
| CN | 105797306 A | 7/2016 | |
| JP | 2011-198184 A | 5/2003 | |
| JP | 2009-87072 A | 4/2009 | |
| JP | 2009-244916 A | 10/2009 | |
| JP | 2013-161315 A | 8/2013 | |
| WO | WO-2005003902 A2 * | 1/2005 | ............... A61B 5/00 |

OTHER PUBLICATIONS

International Search Report for International Application No. PCT/JP2020/006647, dated May 26, 2020.
German Office Action for German Application No. 11 2020 000 692.1, dated Mar. 7, 2023, with English translation.
Chinese Office Action and Search Report for Chinese Application No. 202080018212.6, dated Mar. 25, 2022, with an English translation.

* cited by examiner

[FIG. 1]
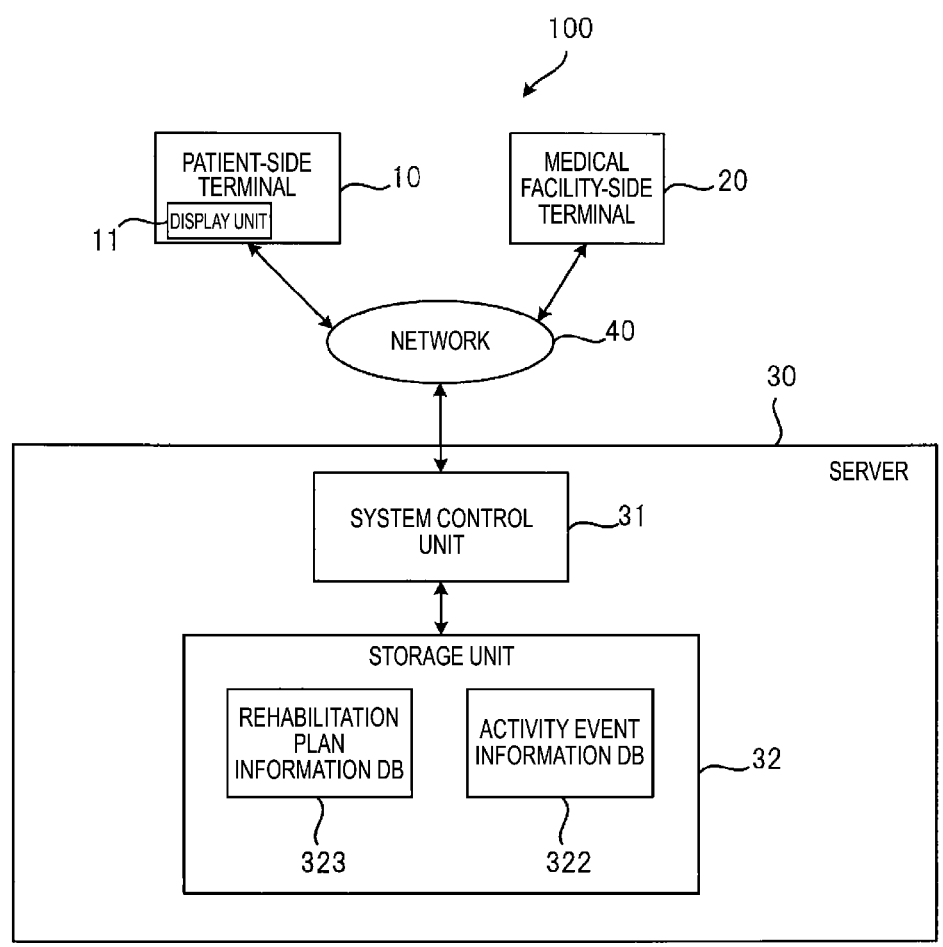

[FIG. 2]

| | ACTIVITY EVENT TYPE | REHABILITATION TARGET PART | EXERCISE AMOUNT |
|---|---|---|---|
| ST1 | CYCLING (1 HOUR) | HAND | ** |
| | | ARM | ** |
| | | SHOULDER | ** |
| | | KNEE | ** |
| | | THIGH | ** |
| | | ANKLE | ** |
| ST2 | CLIMBING (500 M OR HIGHER) | HAND | ** |
| | | ARM | ** |
| | | SHOULDER | ** |
| | | KNEE | ** |
| | | THIGH | ** |
| | | ANKLE | ** |
| ST3 | WALKING (30 MINUTES) | HAND | ** |
| | | ARM | ** |
| | | SHOULDER | ** |
| | | KNEE | ** |
| | | THIGH | ** |
| | | ANKLE | ** |
| ST4 | __ TOUR | HAND | ** |
| | | ARM | ** |
| | | SHOULDER | ** |
| | | KNEE | ** |
| | | THIGH | ** |
| | | ANKLE | ** |
| ST5 | HOSPITAL REHABILITATION | HAND | ** |
| | | ARM | ** |
| | | SHOULDER | ** |
| | | KNEE | ** |
| | | THIGH | ** |
| | | ANKLE | ** |
| ST6 | GOLF | HAND | ** |
| | | ARM | ** |
| | | SHOULDER | ** |
| | | KNEE | ** |
| | | THIGH | ** |
| | | ANKLE | ** |
| ST7 | TABLE TENNIS (1 HOUR) | HAND | ** |
| | | ARM | ** |
| | | SHOULDER | ** |
| | | KNEE | ** |
| | | THIGH | ** |
| | | ANKLE | ** |

[FIG. 3]
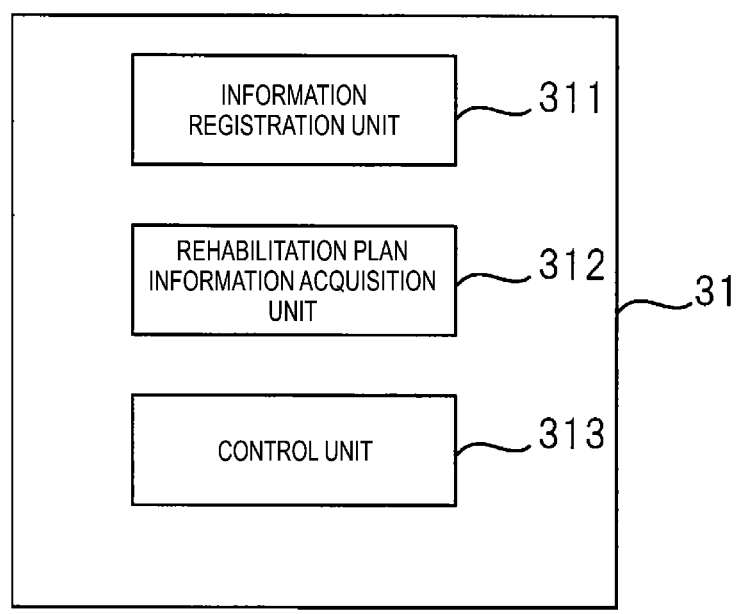

[FIG. 4]

SELECT YOUR PREFERRED ACTIVITY FROM ACTIVITY EVENT LIST BELOW

FULFILLMENT DEGREE OF YOUR WEEKLY REHABILITATION PLAN

KNEE 0 – 100

THIGH 0 – 100

SHOULDER 0 – 100

ACTIVITY EVENT LIST

- 14A — CYCLING 1 HOUR
- 14B — CLIMBING (500 M OR HIGHER)
- 14C — WALKING 30 MINUTES
- 14D — __ TOUR
- 14E — HOSPITAL REHABILITATION
- 14F — GOLF
- 14G — TABLE TENNIS 1 HOUR

[FIG. 5]
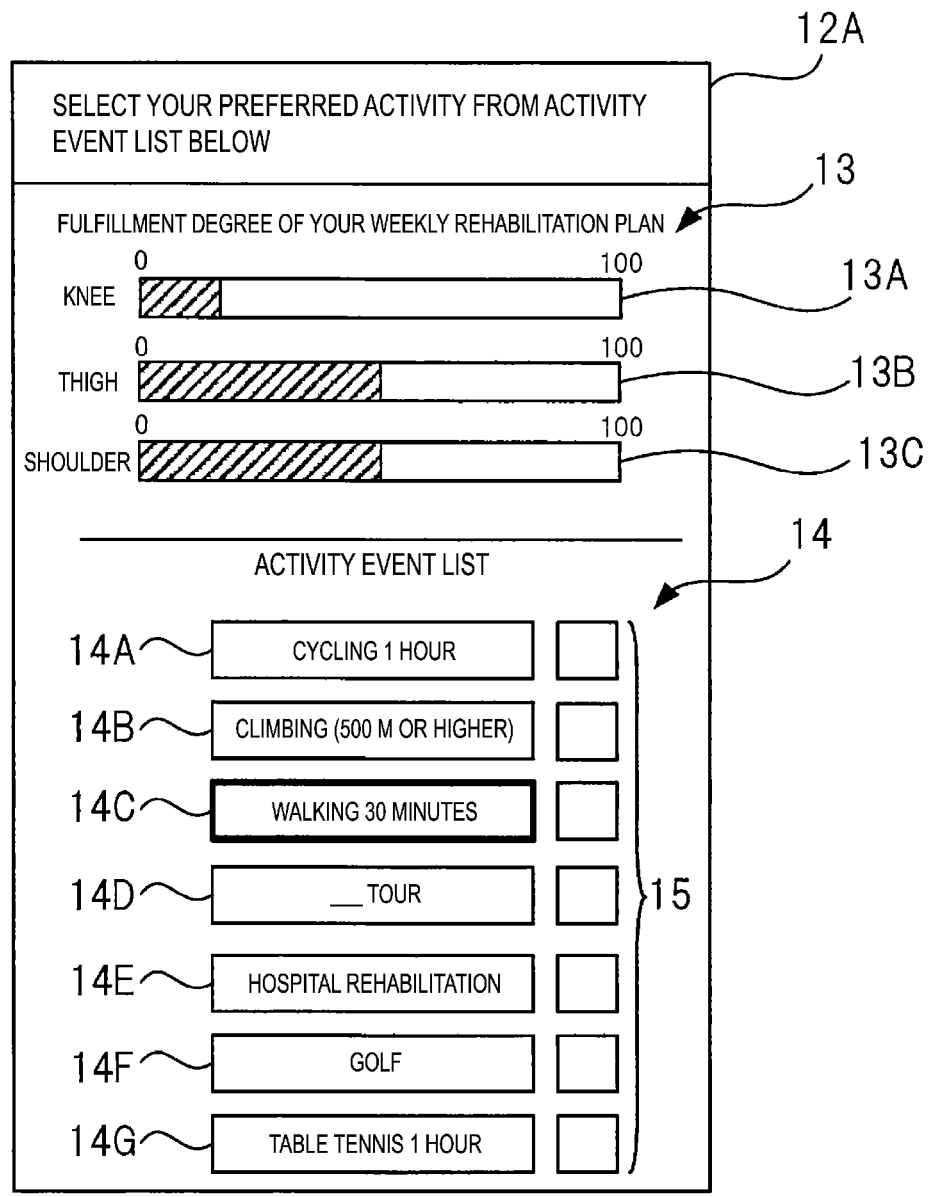

[FIG. 6]

```
SELECT YOUR PREFERRED ACTIVITY FROM ACTIVITY
EVENT LIST BELOW
```
— 12E

FULFILLMENT DEGREE OF YOUR WEEKLY REHABILITATION PLAN — 13

KNEE 0 —— 100 — 13A

THIGH 0 —— 100 — 13B

SHOULDER 0 —— 100 — 13C

ACTIVITY EVENT LIST — 14

| Ref | Activity | |
|---|---|---|
| 14A | CYCLING 1 HOUR | |
| 14B | CLIMBING (500 M OR HIGHER) | |
| 14C | WALKING 30 MINUTES | 2 |
| 14D | __ TOUR | |
| 14E | HOSPITAL REHABILITATION | |
| 14F | GOLF | |
| 14G | TABLE TENNIS 1 HOUR | |

SELECT YOUR PREFERRED ACTIVITY FROM ACTIVITY EVENT LIST BELOW — 12B

FULFILLMENT DEGREE OF YOUR WEEKLY REHABILITATION PLAN — 13

KNEE  0 — 100 — 13A
THIGH 0 — 100 — 13B
SHOULDER 0 — 100 — 13C

ACTIVITY EVENT LIST — 14

- 14A — CYCLING 1 HOUR
- 14B — CLIMBING (500 M OR HIGHER)
- 14C — WALKING 30 MINUTES
- 14D — __ TOUR
- 14E — HOSPITAL REHABILITATION
- 14F — GOLF
- 14G — TABLE TENNIS 1 HOUR

15

[FIG. 8]
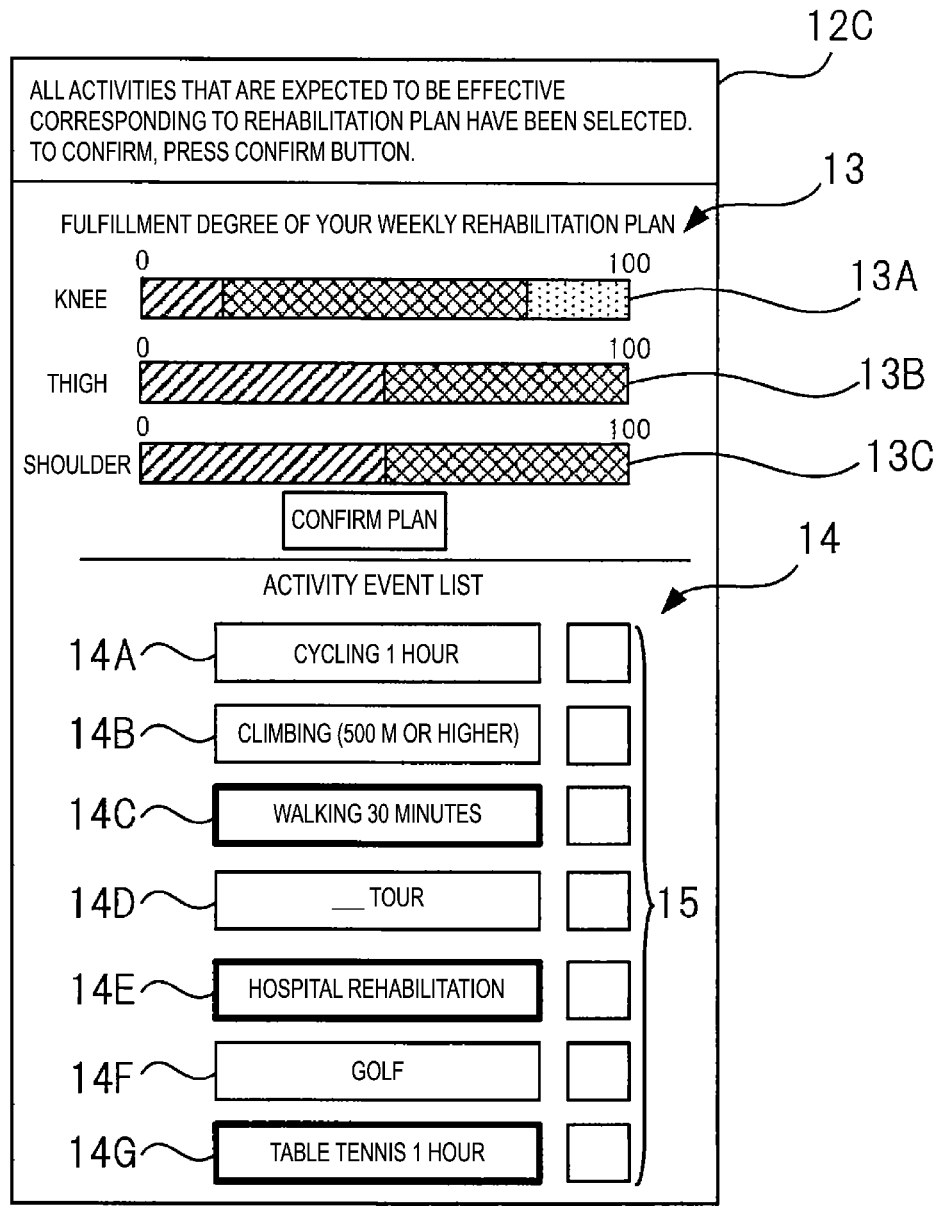

[FIG. 9]
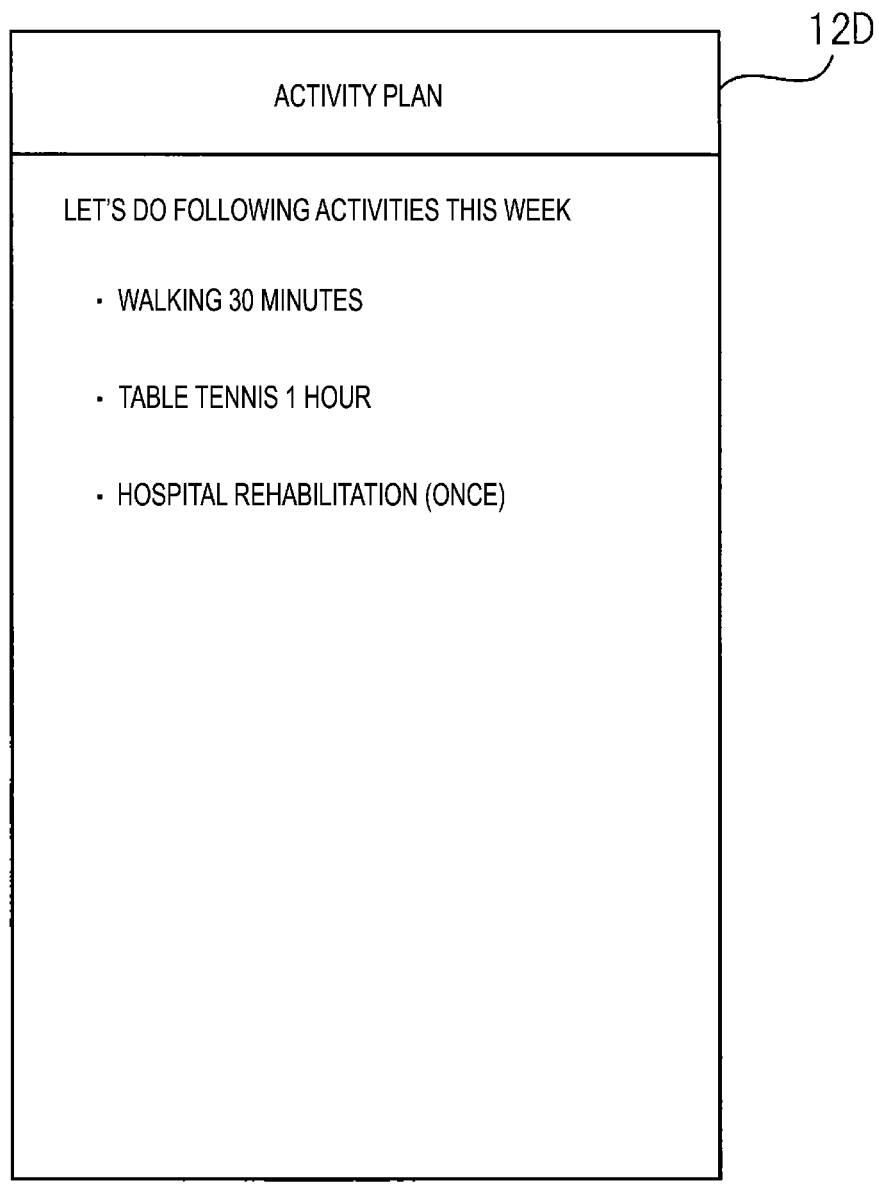

[FIG. 10]
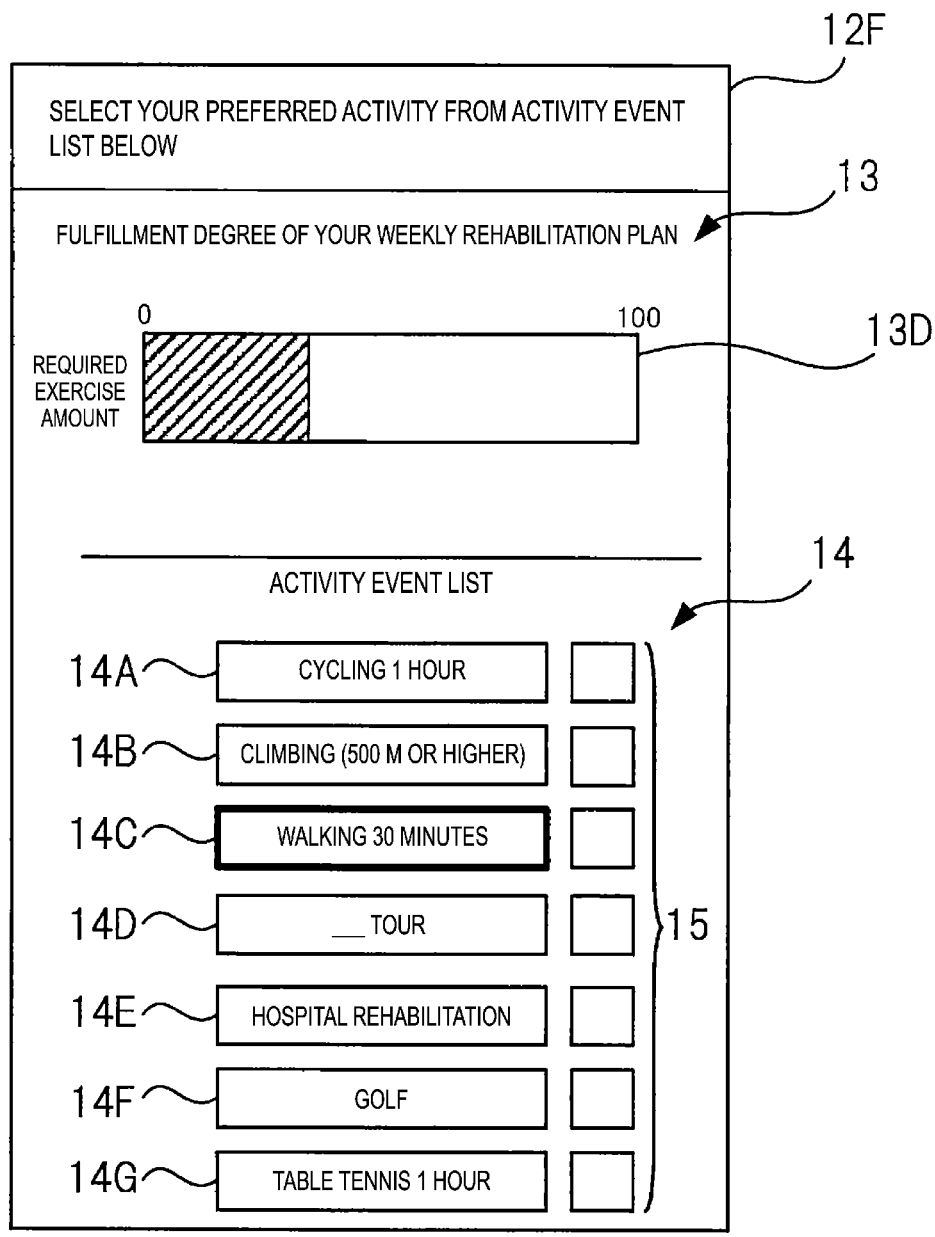

REHABILITATION ASSISTANCE DEVICE, REHABILITATION ASSISTANCE METHOD, AND NON-TRANSIENT STORAGE MEDIUM STORING REHABILITATION ASSISTANCE PROGRAM

CROSS-REFERENCE TO RELATED APPLICATIONS

This application is the U.S. national stage application filed pursuant to 35 U.S.C. 365(c) and 120 as a continuation of International Patent Application No. PCT/JP2020/006647, filed Feb. 19, 2020, which application claims priority to Japanese Patent Application No. 2019-045931, filed Mar. 13, 2019, which applications are incorporated herein by reference in their entireties.

TECHNICAL FIELD

The present invention relates to a rehabilitation assistance device, a rehabilitation assistance method, and a non-transient storage medium storing a rehabilitation assistance program.

BACKGROUND ART

Rehabilitation (aka. rehab) is performed to alleviate mental and physical disorders in addition to helping overcome obstacles in life which are caused by illness, trauma, etc. Therefore, in hospitals, etc., patients and medical professionals such as physical therapists need to work together to plan and execute rehabilitation.

Patent Literature 1 discloses a rehabilitation management device that stores rehabilitation plan data in association with each patient, acquires rehabilitation execution data generated when the patient uses a rehabilitation prosthesis device, and compares the rehabilitation execution data with the rehabilitation plan data to grasp the achievement status of the patient's rehabilitation.

CITATION LIST

Patent Literature

Patent Document 1: JP 2013-161315 A

SUMMARY OF INVENTION

Technical Problem

For people who need rehabilitation for a long period of time, medical institutions alone are not enough to achieve the full effect of the treatment. Therefore, it is important to conduct voluntary rehabilitation at home or the like, other than medical institutions. However, general rehabilitation plans are created by medical institutions, and the contents of these plans are often uninteresting, such as stretching methods or muscle training methods. Therefore, a problem is that it is difficult to increase the patient's motivation to continue rehabilitation. The device described in Patent Document 1 can grasp the achievement status of rehabilitation, but does not consider generation of a rehabilitation plan that can increase the motivation to continue rehabilitation.

The purpose of the present invention is to provide a rehabilitation assistance device, a rehabilitation assistance method, and a rehabilitation assistance program that support continuous rehabilitation by enabling the generation of a rehabilitation plan that can increase the motivation to continue rehabilitation.

Solution to Problem (1) Provided is a rehabilitation assistance device, including:

an activity event information database that stores a plurality of sets that associate information of a predetermined activity event with information of an exercise amount for each of a plurality of body parts when the activity event is performed;

a rehabilitation plan information acquisition unit that acquires rehabilitation plan information specifying an exercise amount required for each of body parts requiring rehabilitation of a rehabilitation subject; and a control unit that, based on the set containing the information of the activity event selected by the rehabilitation subject from among the information of a plurality of the activity events and based on the rehabilitation plan information, generates and outputs display information for displaying to what extent the exercise amount contained in the rehabilitation plan information is achieved by the activity event of the selected set.

According to (1), when selecting an activity event, the rehabilitation subject can check to what extent the exercise amount included in the rehabilitation plan information is achieved by performing the activity event, through the information displayed on the display unit based on the display information. The rehabilitation subject can, by selecting activity events so that all of the exercise amounts included in one's rehabilitation plan information are achieved, for example, make an activity plan consisting only of favorite activity events of one's own. By simply following this activity plan, the rehabilitation subject will be able to achieve the rehabilitation plan naturally without feeling that one is being forced to do rehabilitation. As a result, rehabilitation can be continued.

(2) Provided is the rehabilitation assistance device according to (1), wherein the control unit generates, as the display information, information for displaying to what extent the exercise amount for each of the body parts included in the rehabilitation plan information is achieved by the activity event of the selected set.

According to (2), when selecting an activity event, the rehabilitation subject can check to what extent the exercise amount for each body part included in the rehabilitation plan information is achieved by performing the activity event, through the information displayed on the display unit. This makes it easier to understand how to select activity events to fulfill the rehabilitation plan, and makes the generation of the activity plan more efficient.

(3) Provided is the rehabilitation assistance device according to (1) or (2), wherein the activity events are walking, jogging, running, cycling, climbing, traveling, sports, or hospital rehabilitation.

(4) Provided is a rehabilitation assistance method including: by a computer accessible to an activity event information database storing a plurality of sets that associate information of a predetermined activity event with information of an exercise amount for each of a plurality of body parts when the activity event is performed, acquiring rehabilitation plan information, the rehabilitation plan information specifying an exercise amount required for each of body parts requiring rehabilitation of a rehabilitation subject; and controlling to generate and output, based on the set containing the information of the activity event selected by the rehabilitation subject from among the information of a plurality of the activity events and based on the rehabilitation plan information, display information for displaying to what extent the exercise amount contained in the rehabilitation plan information is achieved by the activity event of the selected set.

(5) Provided is a non-transient storage medium storing a rehabilitation assistance program causing a computer, the computer accessible to an activity event information database storing a plurality of sets that associate information of a predetermined activity event with information of an exercise amount for each of a plurality of body parts when the activity event is performed, to execute:

acquiring rehabilitation plan information, the rehabilitation plan information specifying exercise amount required for each of body parts requiring rehabilitation of a rehabilitation subject; and controlling to generate and output, based on the set containing the information of the activity event selected by the rehabilitation subject from among the information of a plurality of the activity events and based on the rehabilitation plan information, display information for displaying to what extent the exercise amount contained in the rehabilitation plan information is achieved by the activity event of the selected set.

Advantageous Effects of Invention

According to the present invention, a rehabilitation assistance device, a rehabilitation assistance method, and a rehabilitation assistance program can be provided that support continuous rehabilitation by enabling the generation of a rehabilitation plan that can increase the motivation to continue rehabilitation.

BRIEF DESCRIPTION OF DRAWINGS

FIG. 1 is a diagram illustrating a schematic configuration example of a rehabilitation assistance system 100.

FIG. 2 is a schematic diagram illustrating an example of information stored in an activity event information DB 322 of a storage unit 32 illustrated in FIG. 1.

FIG. 3 is a functional block diagram of a system control unit 31 in a server 30 of the rehabilitation assistance system 100 illustrated in FIG. 1.

FIG. 4 is a diagram illustrating an example of a screen displayed on a display unit 11 of the patient-side terminal 10, when the server 30 is accessed from a patient-side terminal 10 used by a patient whose rehabilitation plan information has already been registered in the storage unit 32.

FIG. 5 is a diagram illustrating an example of a screen displayed on the display unit 11 of the patient-side terminal 10 when an icon 14C is selected on a screen 12 illustrated in FIG. 4.

FIG. 6 is a diagram illustrating an example of a screen displayed on the display unit 11 of the patient-side terminal 10 when the icon 14C is selected on the screen 12 illustrated in FIG. 4 and "2" is input to an input field 15 to the right of the icon 14C.

FIG. 7 is a diagram illustrating an example of a screen displayed on the display unit 11 of the patient-side terminal 10 when an icon 14G is further selected on a screen 12A illustrated in FIG. 5.

FIG. 8 is a diagram illustrating an example of a screen displayed on the display unit 11 of the patient-side terminal 10 when an icon 14E is further selected on a screen 12B illustrated in FIG. 7.

FIG. 9 is a diagram illustrating an example of a screen displayed on the display unit 11 of the patient-side terminal 10 when the "Confirm plan" button is selected on a screen 12C illustrated in FIG. 8.

FIG. 10 is a diagram illustrating a modified example of the screen displayed on the display unit 11 of the patient-side terminal 10 when the icon 14C is selected on the screen 12 illustrated in FIG. 4.

DESCRIPTION OF EMBODIMENTS

Outline of Rehabilitation Assistance Device of Embodiments

The rehabilitation assistance device of an embodiment is used, for example, by a rehabilitation subject whose rehabilitation plan information has been created by a doctor or a physical therapist at a medical facility such as a hospital or a facility specializing in rehabilitation. Rehabilitation plan information is information that specifies an exercise amount required for each body part that needs to be rehabilitated in a rehabilitation subject. For example, when the number of times a specific part (joint or muscle) of a rehabilitation subject should be moved in a unit period such as a week is determined, the calorie consumption and the exercise intensity (Mets) in that specific part can be roughly estimated from the number of times. The calorie consumption and exercise intensity approximated in this way are defined as the exercise amount.

Additionally, the rehabilitation assistance device is configured to be able to access an activity event information database that stores a plurality of sets that associate information of a predetermined activity event with information of an exercise amount for each of a plurality of body parts when the activity event is performed. Activity events include walking, jogging, running, cycling, climbing, traveling, sports, hospital rehabilitation, household work including domestic chores (cleaning, cooking, drying laundry, etc.), volunteer activities such as weeding and street cleaning, or hobbies (yoga, tai chi, dancing, fishing, art appreciation, singing, music performance, etc.), or the like. Sports are physical activities in which people compete to win or lose according to certain rules, or seek enjoyment, and include ball games such as golf. Hospital rehabilitation means that a rehabilitation subject visits a medical facility from home and receives rehabilitation at the medical facility.

The rehabilitation assistance device obtains the rehabilitation plan information of the rehabilitation subject from a database or the like, for example. Then, the rehabilitation assistance device generates and outputs, to the display unit, display information for displaying to what extent the exercise amount contained in the rehabilitation plan information is achieved by the activity event of the set selected by the rehabilitation subject, based on the above set containing the information of the activity event selected by the rehabilitation subject from among information of a plurality of the activity events stored in the activity event information database and based on the obtained rehabilitation plan information. The details will be described later, but the display information generated here is, for example, the information for displaying the screen illustrated in FIG. 5. FIG. 5 illustrates an example where the required exercise amount is specified for each of the rehabilitation subject's knees, thighs, and shoulders in the rehabilitation plan information and where the rehabilitation subject selects an activity event of walking for 30 minutes. By walking for 30 minutes, each of the knees, thighs, and shoulders are utilized to generate an exercise amount. The ratio of this exercise amount to a target exercise amount for each part required in the rehabilitation plan information can be grasped by the hatched areas in gauges 13A, 13B, and 13C.

As the rehabilitation subject selects yet another activity event from the state illustrated in FIG. 5, the hatched areas in gauges 13A, 13B, and 13C will increase. The rehabilitation subject can, by ensuring that each of the gauges 13A, 13B, and 13C is filled by a hatched area, for example, make an activity plan consisting only of favorite activity events of one's own. By simply following this activity plan, the rehabilitation subject will be able to achieve the rehabilitation plan naturally without feeling that one is being forced to do rehabilitation. As a result, rehabilitation can be continued.

Overall Configuration of Rehabilitation Assistance System

FIG. 1 illustrates a schematic configuration example of the rehabilitation assistance system 100. As illustrated in FIG. 1, the rehabilitation assistance system 100 includes: the server 30; a network 40 such as the Internet; the patient-side terminal 10 used by patients (rehabilitation subjects) using the system to access the server 30 via the network 40; and a medical facility-side terminal 20 used by the medical facility personnel using the system to access the server 30 via the network 40.

The patient-side terminal 10 and the medical facility-side terminal 20 are electronic devices such as a smartphone, a personal computer, or a tablet-type terminal or the like, which include respectively a display of information using a display unit; an operation interface for inputting information such as a keyboard, a mouse, or a touch panel; and a communication interface for connecting to the network 40. In FIG. 1, the display unit included in the patient-side terminal 10 is indicated by the reference sign 11.

The server 30 includes the system control unit 31 and the storage unit 32 including a device capable of storing information, such as a hard disk drive or a solid state drive (SSD). The server 30 constitutes a rehabilitation assistance device.

The system control unit 31 includes a processor like a Central Processing Unit (CPU), a Random Access Memory (RAM), and a Read Only Memory (ROM) or the like, and performs general control of the entire system according to the program. The ROM of the system control unit 31 stores programs including the rehabilitation assistance program.

The storage unit 32 stores: the rehabilitation plan information DB (database) 323 that is a set of rehabilitation plan information for each patient transmitted from the medical facility-side terminal 20; and the activity event information DB 322.

In this system, a doctor or the like at a medical facility makes a diagnosis of a patient and creates rehabilitation plan information for that patient. When a medical facility personnel operates a medical facility-side terminal 20 and transmits the rehabilitation plan information of the patient to the server 30, the system control unit 31 of the server 30 stores the received rehabilitation plan information in the rehabilitation plan information DB 323 in association with the patient's identification information.

It is also possible to have a configuration in which a patient, who has had rehabilitation plan information created by a doctor, transmits the patient's own identification information and rehabilitation plan information to the server 30 using a patient-side terminal 10, and these are stored in the rehabilitation plan information DB 323.

The rehabilitation plan information is information that specifies the exercise amount required for each body part that needs to be rehabilitated in a patient, as described above. The rehabilitation plan information is information that specifies, for example, that the knees require an exercise amount M1, the thighs require an exercise amount M2, and the shoulders require an exercise amount M3 in a unit period such as one week.

As described above, the activity event information DB 322 stores a plurality of sets that associate information of a predetermined activity event with information of an exercise amount for each of a plurality of body parts when the activity event is performed.

Example of Information Registered in Activity Event Information DB 322

FIG. 2 is a schematic diagram illustrating an example of the information stored in the activity event information DB 322 of the storage unit 32 illustrated in FIG. 1. FIG. 2 illustrates seven sets, from sets ST1 to ST7.

The set ST1 includes the information "Cycling (1 hour)" as the activity event type, indicating that cycling will be performed for 1 hour. In addition, the set ST1 includes multiple pieces of information such as hands, arms, shoulders, knees, thighs, and ankles as rehabilitation target parts, which are body parts to be rehabilitated. Furthermore, the set ST1 includes information on the exercise amount, for each rehabilitation target part, which is assumed to be consumed when cycling for one hour.

The set ST2 includes the information "Climbing (500 m or higher)" as the activity event type, indicating of climbing a mountain having a height of 500 m or higher. Additionally, the set ST2 includes multiple pieces of information such as hands, arms, shoulders, knees, thighs, and ankles as rehabilitation target parts. Furthermore, the set ST2 includes information on the exercise amount, for each rehabilitation target part, which is assumed to be consumed when climbing a mountain having a height of 500 m or higher.

The set ST3 includes the information "Walking (30 minutes)" as the activity event type, indicating that walking will be performed for 30 minutes. Additionally, the set ST3 includes multiple pieces of information such as hands, arms, shoulders, knees, thighs, and ankles as rehabilitation target parts. Furthermore, the set ST3 includes information on the exercise amount, for each rehabilitation target part, which is assumed to be consumed when walking for 30 minutes.

The set ST4 includes the information "_____ tour" as the activity event type, indicating that the user will participate in a trip planned by a system administrator. Additionally, the set ST4 includes multiple pieces of information such as hands, arms, shoulders, knees, thighs, and ankles as rehabilitation target parts. Furthermore, the set ST4 includes information on the exercise amount, for each rehabilitation target part, which is assumed to be consumed when participating in the trip identified by the activity event type.

The set ST5 includes the information of "Hospital rehabilitation" as the activity event type, indicating that hospital rehabilitation is performed. The set ST5 includes multiple pieces of information such as hands, arms, shoulders, knees, thighs, and ankles as rehabilitation target parts. Furthermore, the set ST5 includes information on the exercise amount, for each rehabilitation target part, which is assumed to be consumed when the hospital rehabilitation is performed.

The set ST6 includes the information of "Golf" as the activity event type, indicating that golf is played. The set ST6 includes multiple pieces of information such as hands, arms, shoulders, knees, thighs, and ankles as rehabilitation target parts. Furthermore, the set ST6 includes information on the exercise amount, for each rehabilitation target part, which is assumed to be consumed when playing golf.

Set ST7 includes the information of "Table tennis (1 hour)" as the activity event type, indicating that table tennis will be played for 1 hour. The set ST7 includes multiple pieces of information such as hands, arms, shoulders, knees, thighs, and ankles as rehabilitation target parts. Furthermore, the set ST7 includes information on the exercise amount, for each rehabilitation target part, which is assumed to be consumed when playing table tennis for one hour.

The exercise amount for each rehabilitation target part in each set can vary depending on the patient's weight and age or the like. Therefore, the sets ST1 to ST7 may be generated separately for each patient's identification information and stored in the activity event information DB 322.

Function of Control Unit in Server

FIG. 3 is a functional block diagram of the system control unit 31 in the server 30 of the rehabilitation assistance system 100 illustrated in FIG. 1. The processor of the system control unit 31 functions as an information registration unit 311, a rehabilitation plan information acquisition unit 312, and a control unit 313, by executing the above rehabilitation assistance program stored in ROM.

When patient's rehabilitation plan information and the patient's identification information are transmitted from the medical facility-side terminal 20, the information registration unit 311 stores them in the rehabilitation plan information DB 323 in association with each other.

The rehabilitation plan information acquisition unit 312 acquires the rehabilitation plan information corresponding to this identification information from the storage unit 32 when there is a request from the patient-side terminal 10 used by a patient identified by identification information of any patient registered in the rehabilitation plan information DB 323.

The control unit 313 generates and transmits, to the patient-side terminal 10 that has made the request, first display information for displaying the screen illustrated in FIG. 4, for example, based on the rehabilitation plan information acquired by the rehabilitation plan information acquisition unit 312 and based on the information stored in the activity event information DB 322.

FIG. 4 is a diagram illustrating an example of a screen displayed on the display unit 11 of the patient-side terminal 10 when the server 30 is accessed from the patient-side terminal 10 used by a patient whose rehabilitation plan information has already been registered in the storage unit 32.

The screen 12 illustrated in FIG. 4 includes: a first area 13 where images based on the rehabilitation plan information are displayed; and a second area 14 where images based on the information stored in the activity event information DB 322 are displayed. FIG. 4 illustrates an example of a screen where the rehabilitation plan information specifies a target exercise amount for each body part, for example, knees, thighs, and shoulders in one week. The target exercise amount of the knees included in the rehabilitation plan information is, for example, 1000 kcal, the target exercise amount of the thighs included in the rehabilitation plan information is, for example, 400 kcal, and the target exercise amount of the shoulders included in the rehabilitation plan information is, for example, 100 kcal.

The first area 13 illustrates the gauges 13A, 13B, and 13C corresponding to each of the knees, thighs, and shoulders as body parts included in the rehabilitation plan information. The gauges 13A, 13B, and 13C are for visualizing the fulfillment degree of the target exercise amount, with the target exercise amount in the plan corresponding to each of them being 100.

The second area 14 displays icons 14A to 14G corresponding to each of the sets ST1 to ST7 stored in the activity event information DB 322, and seven of the input fields 15 for inputting the number of times.

The icon 14A is an icon that indicates an activity event type of the set ST1. The icon 14B is an icon that indicates an activity event type of the set ST2. The icon 14C is an icon that indicates an activity event type of the set ST3. The icon 14D is an icon that indicates an activity event type of the set ST4. The icon 14E is an icon that indicates an activity event type of the set ST5. The icon 14F is an icon that indicates an activity event type of the set ST6. The icon 14G is an icon that indicates an activity event type of the set ST7.

The input field 15 to the right of each of the icons 14A to 14G is for inputting one or more natural numbers. Each of the icons 14A to 14G can be "Selected" and "Deselected" by touch operation, for example. When any icon is selected, and the number inputted in the input field 15 to the right of the icon is "2", it means that the icon has been selected "2" times.

When the screen 12 illustrated in FIG. 4 is displayed on the display unit 11, the patient freely selects any icon from the second area 14 of the screen 12 to determine a combination of activity events that can achieve all the target exercise amounts included in one's rehabilitation plan information. For example, the operation when the patient selects the icon 14C from the state of FIG. 4 will be described.

When the patient selects the icon 14C, the control unit 313 generates and transmits (outputs), to the patient-side terminal 10, second display information for displaying to what extent the total exercise amount contained in the rehabilitation plan information is achieved by the activity events contained in the selected set ST3, based on the set ST3 corresponding to the icon 14C and based on the rehabilitation plan information of the patient.

FIG. 5 is a diagram illustrating an example of a screen displayed on the display unit 11 of the patient-side terminal 10 when the icon 14C is selected on the screen 12 illustrated in FIG. 4. FIG. 5 illustrates the screen 12A displayed on the display unit 11 of the patient-side terminal 10 based on the second display information transmitted from the control unit 313.

In the screen 12A, the icon 14C has been changed to a bold frame display to illustrate that the icon 14C is selected. In the screen 12A, each of the gauges 13A, 13B, and 13C is indicated by a hatched bar.

The bar displayed on the gauge 13A indicates, by its length, what percentage of the target exercise amount associated with the knees will be achieved when the user performs the activity event of the set ST3 corresponding to the selected icon 14C. For example, when the exercise amount corresponding to the knees included in the set ST3 is 200 kcal, 20% of the target exercise amount (1000 kcal) associated with the knees is achieved when the user performs the activity event of the set ST3. Therefore, the control unit 313 displays a bar with a length of 20% of the maximum value (100) on the gauge 13A of the screen 12A in FIG. 5.

The bar displayed on the gauge 13B indicates, by its length, what percentage of the target exercise amount associated with the thighs will be achieved when the user performs the activity event of the set ST3 corresponding to the selected icon 14C. For example, when the exercise amount corresponding to the thigh included in the set ST3 is 200 kcal, 50% of the target exercise amount (400 kcal) associated with the thighs is achieved when the user performs the activity event of the set ST3. Therefore, the control unit 313 displays a bar with a length of 50% of the maximum value on the gauge 13B of the screen 12A in FIG. 5.

The bar displayed on the gauge 13C indicates, by its length, what percentage of the target exercise amount associated with the shoulders will be achieved when the user performs the activity event of the set ST3 corresponding to the selected icon 14C. For example, when the exercise amount corresponding to the shoulder included in the set ST3 is 50 kcal, 50% of the target exercise amount (100 kcal) associated with the shoulders is achieved when the user performs the activity event of the set ST3. Therefore, the control unit 313 displays a bar with a length of 50% of the maximum value on the gauge 13C of the screen 12A in FIG. 5.

FIG. 6 is a diagram illustrating an example of a screen displayed on the display unit 11 of the patient-side terminal 10 when the icon 14C is selected on the screen 12 illustrated in FIG. 4 and "2" is input to the input field 15 to the right of the icon 14C. FIG. 6 illustrates the screen 12E displayed on the display unit 11 of the patient-side terminal 10 based on the second display information transmitted from the control unit 313.

The bar displayed on the gauge 13A in the screen 12E indicates, by its length, what percentage of the target exercise amount associated with the knees will be achieved when the user performs twice the activity event of the set ST3 corresponding to the selected icon 14C. For example, when the exercise amount corresponding to the knees included in the set ST3 is 200 kcal, 40% of the target exercise amount (1000 kcal) associated with the knees is achieved when the user performs twice the activity event of the set ST3. Therefore, the control unit 313 displays a bar with a length of 40% of the maximum value on the gauge 13A of the screen 12E in FIG. 6.

The bar displayed on the gauge 13B in the screen 12E indicates, by its length, what percentage of the target exercise amount associated with the thighs will be achieved when the user performs twice the activity event of the set ST3 corresponding to the selected icon 14C. For example, when the exercise amount corresponding to the thighs included in the set ST3 is 200 kcal, 100% of the target exercise amount (400 kcal) associated with the thighs is achieved when the user performs twice the activity event of the set ST3. Therefore, the control unit 313 displays a bar with a length of 100% of the maximum value on the gauge 13B of the screen 12E in FIG. 6.

The bar displayed on the gauge 13C in the screen 12E indicates, by its length, what percentage of the target exercise amount associated with the shoulders will be achieved when the user performs twice the activity event of the set ST3 corresponding to the selected icon 14C. For example, when the exercise amount corresponding to the shoulders included in the set ST3 is 50 kcal, 100% of the target exercise amount (100 kcal) associated with the shoulders is achieved when the user performs twice the activity event of the set ST3. Therefore, the control unit 313 displays a bar with a length of 100% of the maximum value on the gauge 13C of the screen 12E in FIG. 6.

Next, when the patient selects the icon 14G in the screen 12A illustrated in FIG. 5, the control unit 313 generates and transmits (outputs), to the patient-side terminal 10, second display information for displaying to what extent the total exercise amount contained in the rehabilitation plan information is achieved by the activity events contained in the selected set ST3 and ST7, based on: the set ST7 corresponding to the icon 14G; the rehabilitation plan information of the patient; and the set ST3 corresponding to the icon 14C that is already selected.

FIG. 7 is a diagram illustrating an example of a screen displayed on the display unit 11 of the patient-side terminal 10 when the icon 14G is further selected on the screen 12A illustrated in FIG. 5. FIG. 7 illustrates the screen 12B displayed on the display unit 11 of the patient-side terminal 10 based on the second display information transmitted from the control unit 313.

In the screen 12B, the icon 14G has been changed to a bold frame display to illustrate that the icon 14G is selected. In the screen 12B, each of the gauges 13A, 13B, and 13C has a differently hatched bar than in FIG. 5.

A new bar displayed on the gauge 13A indicates, by its length, what percentage of the target exercise amount associated with the knees will be achieved when the user performs the activity event of the set ST7 corresponding to the selected icon 14G. For example, when the exercise amount corresponding to the knees included in the set ST7 is 600 kcal, 60% of the target exercise amount (1000 kcal) associated with the knees is achieved when the user performs the activity event of the set ST7. Therefore, the control unit 313 additionally displays a bar with a length of 60% of the maximum value on the gauge 13A of the screen 12B in FIG. 7.

A new bar displayed on the gauge 13B indicates, by its length, what percentage of the target exercise amount associated with the thighs will be achieved when the user performs the activity event of the set ST7 according to the selected icon 14G. For example, when the exercise amount corresponding to the thighs included in the set ST7 is 200 kcal, 50% of the target exercise amount (400 kcal) associated with the thighs is achieved when the user performs the activity event of the set ST7. Therefore, the control unit 313 additionally displays a bar with a length of 50% of the maximum value on the gauge 13B of the screen 12B in FIG. 7. The bar displayed on each of the gauges 13A, 13B, and 13C are controlled so that their length is at most the same as the length of each gauge.

A new bar displayed on the gauge 13C indicates, by its length, what percentage of the target exercise amount associated with the shoulders will be achieved when the user performs the activity event of the set ST7 corresponding to the selected icon 14G. For example, when the exercise amount corresponding to the shoulder included in the set ST7 is 50 kcal, 50% of the target exercise amount (100 kcal) associated with the shoulders is achieved when the user performs the activity event of the set ST7. Therefore, the control unit 313 additionally displays a bar with a length of 50% of the maximum value on the gauge 13C of the screen 12B in FIG. 7.

Next, when the patient selects the icon 14E in the screen 12B illustrated in FIG. 7, the control unit 313 generates and transmits (outputs), to the patient-side terminal 10, second display information for displaying to what extent the total exercise amount contained in the rehabilitation plan information is achieved by the activity events contained in the selected set ST3, ST5, and ST7, based on: the set ST5 corresponding to the icon 14E; the rehabilitation plan information of the patient; the set ST3 corresponding to the icon 14C already selected; and the set ST7 corresponding to the icon 14G that is already selected.

FIG. 8 is a diagram illustrating an example of a screen displayed on the display unit 11 of the patient-side terminal 10 when the icon 14E is further selected on the screen 12B illustrated in FIG. 7. FIG. 8 illustrates the screen 12C displayed on the display unit 11 of the patient-side terminal 10 based on the second display information transmitted from the control unit 313.

In the screen 12C, the icon 14E has been changed to a bold frame display to illustrate that the icon 14E is selected. In the screen 12C, the gauge 13A has a differently hatched bar than in FIGS. 5 and 7.

The new bar displayed on the gauge 13A indicates, by its length, what percentage of the target exercise amount associated with the knees will be achieved when the user performs the activity event of the set ST5 associated with the selected icon 14E. For example, when the exercise amount corresponding to the knees included in the set ST5 is 200 kcal, 20% of the target exercise amount (1000 kcal) associated with the knees is achieved when the user performs the activity event of the set ST5. Therefore, the control unit 313 additionally displays a bar with a length of 20% of the maximum value on the gauge 13A of the screen 12C in FIG. 8.

In the screen 12C illustrated in FIG. 8, the gauges 13A, 13B, and 13C are filled by bars, respectively. In other words, the three activity events selected by the patient are in a state to achieve the total exercise amount contained in the rehabilitation plan information for that patient. In this state, the control unit 313 displays a "Confirm plan" button on the screen 12C, and further displays a message of "All activities that are expected to be effective corresponding to rehabilitation plan have been selected. To confirm, press Confirm button.".

When the patient selects the "Confirm plan" button included in the screen 12C, a confirmation request is transmitted from the patient-side terminal 10 to the server 30. When receiving this confirmation request, the control unit 313 generates and transmits, to the patient-side terminal 10, third display information for displaying a list of the contents of the activity events included in the sets ST3, ST5, and ST7 selected by the patient.

FIG. 9 illustrates an example of a screen displayed on the display unit 11 of the patient-side terminal 10 when the "Confirm plan" button is selected on the screen 12C illustrated in FIG. 8. FIG. 9 illustrates a screen 12D displayed on the display unit 11 of the patient-side terminal 10 based on the third display information transmitted from the control unit 313. The patients store the screen 12D illustrated in FIG. 9 by saving or printing, and spend one week according to this activity plan.

Effect of Rehabilitation Assistance System 100

As described above, according to the rehabilitation assistance system 100, when the patient selects an activity event, the patient can check, by performing the activity event, to what extent the exercise amount included in the rehabilitation plan information is achieved by the screen (screen 12A, 12B, 12C, 12E) displayed on the display unit 11 based on the second display information. The patient can, by selecting activity events so that all of the exercise amounts included in one's rehabilitation plan information are achieved, for example, make an activity plan consisting only of favorite activity events of one's own. By simply following this activity plan, patients will be able to achieve their rehabilitation plan naturally without feeling that they are being forced to do rehabilitation. As a result, rehabilitation can be continued.

Also, according to the rehabilitation assistance system 100, when the patient selects an activity event, the patient can check, by the bars of the respective gauges 13A, 13B, and 13C displayed on the display unit 11, to what extent the exercise amount for each body part included in the rehabilitation plan information will be achieved by performing the activity event. This makes it easier to understand how to select activity events to fulfill the rehabilitation plan, and makes the generation of the activity plan more efficient.

Modified Example of Rehabilitation Assistance System 100

FIG. 10 is a diagram illustrating a modified example of a screen displayed on the display unit 11 of the patient-side terminal 10 when the icon 14C is selected on the screen 12 illustrated in FIG. 4. FIG. 10 illustrates a screen 12F displayed on the display unit 11 of the patient-side terminal 10 based on the second display information transmitted from the control unit 313.

In the screen 12F, the icon 14C has been changed to a bold frame display to illustrate that the icon 14C is selected. A gauge 13D is also displayed in the first area 13 of the screen 12F. The gauge 13D is used to visualize the fulfillment degree of a total required exercise amount, by defining, as 100, the accumulated value of the exercise amounts included in the patient's rehabilitation plan information, that is, the total required exercise amount.

The bar displayed on the gauge 13D indicates, by its length, what percentage of the accumulated value of the exercise amounts corresponding to each of the knees, thighs, and shoulders will be achieved if the user performs the activity event of the set ST3 corresponding to the selected icon 14C. When the exercise amount corresponding to the knees included in the set ST3 is, for example, 200 kcal, the exercise amount corresponding to the thighs included in the set ST3 is, for example, 100 kcal, and the exercise amount corresponding to the shoulders included in the set ST3 is, for example, 50 kcal, about 30% of the total required exercise amount (1300 kcal) is achieved when the user performs the activity event of the set ST3. Therefore, the control unit 313 displays a bar with a length of 30% of the maximum value on the gauge 13D of the screen 12F in FIG. 10.

In this way, the screen 12F may allow the user to check to what extent the exercise amount will be achieved by the selected activity event with respect to the total required exercise amount included in the rehabilitation plan information.

In the above explanation, the number of sets stored in the activity event information DB 322 is set to seven, but this number of sets can be two or more. In practice, it is preferable that a large number of sets, such as ten or a hundred units, may be stored in the activity event information DB 322. The greater the number of sets, the more options the patient has, and the more motivated the patient is to continue rehabilitation.

In addition, although the foregoing description assumes that the patient operates the patient-side terminal 10, such as at home, to generate an activity plan, the present invention is not limited thereto. The server 30 is a device installed in a medical facility, and the display unit is connected to this device. The patient may then directly operate the device at the medical facility to select an activity event, and the screen displayed on the display unit may change as illustrated in FIG. 4 to FIG. 10 in response to the operation.

Although various embodiments have been described above with reference to the drawings, it goes without saying that the present invention is not limited to such examples. It will be apparent to those skilled in the art that various changes and modifications can be made within the scope of the claims, and it is understood that these are naturally belong within the technical scope of the present invention. Further, each of the components of the above-described embodiments may be combined as desired within a range that does not depart from the spirit of the present invention.

Note that the present application is based on Japanese Patent Application filed Mar. 13, 2019 (JP 2019-045931), the contents of which are incorporated herein by reference.

REFERENCE SIGNS LIST

100 Rehabilitation assistance system
10 Patient-side terminal
11 Display unit
12, 12A to 12F Screen
13 First area
13A, 13B, 13C, 13D Gauge
14 Second area
14A to 14G Icon
15 Input field
20 Medical facility-side terminal
30 Server
31 System control unit
311 Information registration unit
312 Rehabilitation plan information acquisition unit
313 Control unit
32 Storage unit
322 Activity event information DB
323 Rehabilitation plan information DB
ST1 to ST7 Set

The invention claimed is:

1. A rehabilitation assistance device comprising:
an activity event information database that stores a plurality of sets that associate information of a predetermined activity event with information of an exercise amount for each of a plurality of body parts when the activity event is performed; and
a processor configured to:
acquire rehabilitation plan information from the activity event information database specifying an exercise amount required for each of body parts requiring rehabilitation of a rehabilitation subject;
receive a selection, via a graphical user interface, of at least one predetermined activity event for exercise of at least one of the plurality of body parts, and a number of times the at least one predetermined activity event is to be performed,
determine, by accessing information stored in the activity event information database, information indicating to what extent the exercise amount contained in the rehabilitation plan is achieved based on the selected at least one predetermined activity event for exercise of the at least one of the plurality of body parts, and
based on the set containing the information of the activity event selected by the rehabilitation subject from among the information of a plurality of the activity events and based on the rehabilitation plan information, generate and output display information for displaying the determined information indicating to what extent the exercise amount contained in the rehabilitation plan information is achieved by the selected at least one predetermined activity event for exercise of the at least one of the plurality of body parts.

2. The rehabilitation assistance device according to claim 1, wherein
the processor is further configured to generate, as the display information, information for displaying to what extent the exercise amount for each of the body parts included in the rehabilitation plan information is achieved by the activity event of the selected set.

3. The rehabilitation assistance device according to claim 1, wherein
the activity events are walking, jogging, running, cycling, climbing, traveling, sports, or hospital rehabilitation.

4. A rehabilitation assistance method comprising:
by a computer accessible to an activity event information database storing a plurality of sets that associate information of a predetermined activity event with information of an exercise amount for each of a plurality of body parts when the activity event is performed,
acquiring, via the computer, rehabilitation plan information from the activity event information database, the rehabilitation plan information specifying an exercise amount required for each of body parts requiring rehabilitation of a rehabilitation subject;
receiving a selection, via a graphical user interface, of at least one predetermined activity event for exercise of at least one of the plurality of body parts, and a number of times the at least one predetermined activity event is to be performed,
determining, via the computer, by accessing information stored in the activity event information database, information indicating to what extent the exercise amount contained in the rehabilitation plan is achieved based on the selected at least one predetermined activity event for exercise of the at least one of the plurality of body parts, and
controlling, via the computer, to generate and output, based on the set containing the information of the activity event selected by the rehabilitation subject from among the information of a plurality of the activity events and based on the rehabilitation plan information, display information for displaying the determined information indicating to what extent the exercise amount contained in the rehabilitation plan information is achieved by the selected at least one predetermined activity event for exercise of the at least one of the plurality of body parts.

5. A non-transient storage medium storing a rehabilitation assistance program causing a computer, the computer accessible to an activity event information database storing a plurality of sets that associate information of a predetermined activity event with information of an exercise amount for each of a plurality of body parts when the activity event is performed, to execute:
acquiring, via the computer, rehabilitation plan information from an activity event information database, the rehabilitation plan information specifying an exercise amount required for each of body parts requiring rehabilitation of a rehabilitation subject;
receiving a selection, via a graphical user interface, of at least one predetermined activity event for exercise of at least one of the plurality of body parts, and a number of times the at least one predetermined activity event is to be performed,
determining, via the computer, by accessing information stored in the activity event information database, information indicating to what extent the exercise amount contained in the rehabilitation plan is achieved based on the selected at least one predetermined activity event for exercise of the at least one of the plurality of body parts, and
controlling, via the computer, to generate and output, based on the set containing the information of the activity event selected by the rehabilitation subject from among the information of a plurality of the activity events and based on the rehabilitation plan information, display information for displaying the determined information indicating to what extent the exercise amount contained in the rehabilitation plan information is achieved by the selected at least one predetermined activity event for exercise of the at least one of the plurality of body parts.

\* \* \* \* \*